(12) United States Patent
    Martino et al.

(10) Patent No.:  US 12,636,353 B2
(45) Date of Patent:  May 26, 2026

(54) APPLICATION OF MICROBIAL GLYCOSIDASE AS AN ANTI-VIRAL THERAPEUTIC, PROGNOSTIC, AND DIAGNOSTIC

(71) Applicant: THE REGENTS OF THE UNIVERSITY OF CALIFORNIA, Oakland, CA (US)

(72) Inventors: Cameron Martino, La Jolla, CA (US); Benjamin Kellman, La Jolla, CA (US); Nathan Lewis, La Jolla, CA (US); Robin Knight, La Jolla, CA (US); Jeffrey D. Esko, La Jolla, CA (US); Daniel Sandoval, La Jolla, CA (US); Thomas Mandel Clausen, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 282 days.

(21) Appl. No.: 18/005,816

(22) PCT Filed: Aug. 16, 2021

(86) PCT No.: PCT/US2021/046144
    § 371 (c)(1),
    (2) Date: Jan. 20, 2023

(87) PCT Pub. No.: WO2022/040090
    PCT Pub. Date: Feb. 24, 2022

(65) Prior Publication Data
    US 2023/0277634 A1    Sep. 7, 2023

Related U.S. Application Data

(60) Provisional application No. 63/066,428, filed on Aug. 17, 2020.

(51) Int. Cl.
    *A61K 38/51*        (2006.01)
    *A61K 35/74*        (2015.01)
    (Continued)

(52) U.S. Cl.
    CPC .............. *A61K 38/51* (2013.01); *A61K 35/74* (2013.01); *A61K 38/465* (2013.01); *A61P 31/14* (2018.01);
    (Continued)

(58) Field of Classification Search
    CPC ...... A61K 38/51; A61K 35/74; A61K 38/465; A61P 31/14; C12Q 1/02; C12Q 1/34;
    (Continued)

(56) References Cited

U.S. PATENT DOCUMENTS 8,529,889 B2 *  9/2013  Chandrasekaran .... A61K 38/45
                                              514/56
2003/0235890 A1  12/2003  Wyllie et al.
                        (Continued)

FOREIGN PATENT DOCUMENTS

WO      2009126652 A2    10/2009
WO      2015003001 A1    1/2015

OTHER PUBLICATIONS

Khanna, Mayank, et al. "Is host heparanase required for the rapid spread of heparan sulfate binding viruses?." Virology 529 (2019): 1-6. (Year: 2019).*

(Continued)

*Primary Examiner* — Louise W Humphrey
*Assistant Examiner* — Candice Lee Swift
(74) *Attorney, Agent, or Firm* — Eversheds-Sutherland (US) LLP

(57)    ABSTRACT

Methods and compositions for diagnosing, preventing or treating a viral infection in a subject comprising administering to a subject in need thereof an effective amount of a
(Continued)

glycosidase or a sulfatase to degrade a glycan, such as heparan sulfate, to inhibit viral infection, such as COVID-19. Methods for identifying a glycosidase, a sulfatase, or a microbe associated with increased susceptibility to viral infection in a subject.

5 Claims, 8 Drawing Sheets

(51) Int. Cl.

| | | |
|---|---|---|
| *A61K 38/46* | (2006.01) | |
| *A61P 31/14* | (2006.01) | |
| *C12Q 1/02* | (2006.01) | |
| *C12Q 1/34* | (2006.01) | |
| *C12Q 1/527* | (2006.01) | |

(52) U.S. Cl.
CPC .................. *C12Q 1/02* (2013.01); *C12Q 1/34* (2013.01); *C12Q 1/527* (2013.01); *C12Y 301/06013* (2013.01); *C12Y 301/06014* (2013.01); *C12Y 402/02007* (2013.01)

(58) Field of Classification Search
CPC ............ C12Q 1/527; C12Y 301/06013; C12Y 301/06014; C12Y 402/02007
See application file for complete search history.

(56) References Cited

U.S. PATENT DOCUMENTS

| | | |
|---|---|---|
| 2007/0098708 A1 | 5/2007 | Myette |
| 2014/0356855 A1 | 12/2014 | Crawford et al. |
| 2015/0238580 A1 | 8/2015 | Kline |
| 2016/0186168 A1 | 6/2016 | Enevolv |

OTHER PUBLICATIONS

Brenda; https://www.brenda-enzymes.org/enzyme.php?ecno=3.2.1.166#SYNONYM; accessed Jan. 14, 2024 (Year: 2024).*
Griffin, Laura S., and Tracey M. Gloster. "The enzymatic degradation of heparan sulfate." Protein and peptide letters 24.8 (2017): 710-722. (Year: 2017).*

Clausen, Thomas Mandel, et al. "SARS-CoV-2 infection depends on cellular heparan sulfate and ACE2." bioRxiv 2020.07.14.201616; doi: https://doi.org/10.1101/2020.07.14.201616 (Year: 2020).*
Bhattacharyya, Sumit, Kumar Kotlo, and Joanne K. Tobacman. "Increased Expression of Chondroitin Sulfotransferases following AngII may Contribute to Pathophysiology Underlying Covid-19 Respiratory Failure: Impact may be Exacerbated by Decline in Arylsulfatase B Activity." bioRxiv (2020): Jun. 2020. (Year: 2020).*
Sun J, Barbeau B, Sato S, Tremblay MJ. Neuraminidase from a bacterial source enhances both HIV-1-mediated syncytium formation and the virus binding/entry process. Virology. May 25, 2001;284(1):26-36. (Year: 2001).*
Chang J, Block TM, Guo JT. Antiviral therapies targeting host ER alpha-glucosidases: current status and future directions. Antiviral Res. Sep. 2013;99(3):251-60. doi: 10.1016/j.antiviral.2013.06.011. Epub Jun. 29, 2013. (Year: 2013).*
Parra-Rojas C, Nguyen VK, Hernandez-Mejia G, Hernandez-Vargas EA. Neuraminidase Inhibitors in Influenza Treatment and Prevention Is It Time to Call It a Day? Viruses. Aug. 25, 2018;10(9):454. (Year: 2018).*
Brenda heparin lyase; https://brenda-enzymes.org/enzyme.php?ecno=4.2.2.7; accessed Mar. 12, 2025 (Year: 2025).*
Cosma et al., Clin Diagn Lab Immunol. Mar. 2004;11(2):406-10) (Year: 2004).*
Jansson-Löfmark, Rasmus, Stephan Hjorth, and Johan Gabrielsson. "Does in vitro potency predict clinically efficacious concentrations?." Clinical Pharmacology & Therapeutics 108.2 (2020): 298-305. (Year: 2020).*
Laine, Roger A. "The case for re-examining glycosylation inhibitors, mimetics, primers and glycosylation decoys as antivirals and anti-inflammatoires in COVID19." Glycobiology 30.10 (2020): 763-767. (Year: 2020).*
International Search Report and the Written Opinion for International Application No. PCT/US2021/046144, mailed Nov. 24, 2021.
Martino et al. "Bacterial modification of the host glycosaminoglycan heparan sulfate modulates SARS-CoV-2 infectivity," bioRxiv. Aug. 18, 2020.
Chang, et al., Sialidase fusion protein protects against influenza infection in a cigarette smoke-induced model of COPD, Mucosal Immunology, 18 (2025) 467-480.
Malakhov, et al., Sialidase Fusion Protein as a Novel Broad-Spectrum Inhibitor of Influenza Virus Infection, Antimicrobial Agents and Chemotherapy (2006) 1470-1479.

* cited by examiner

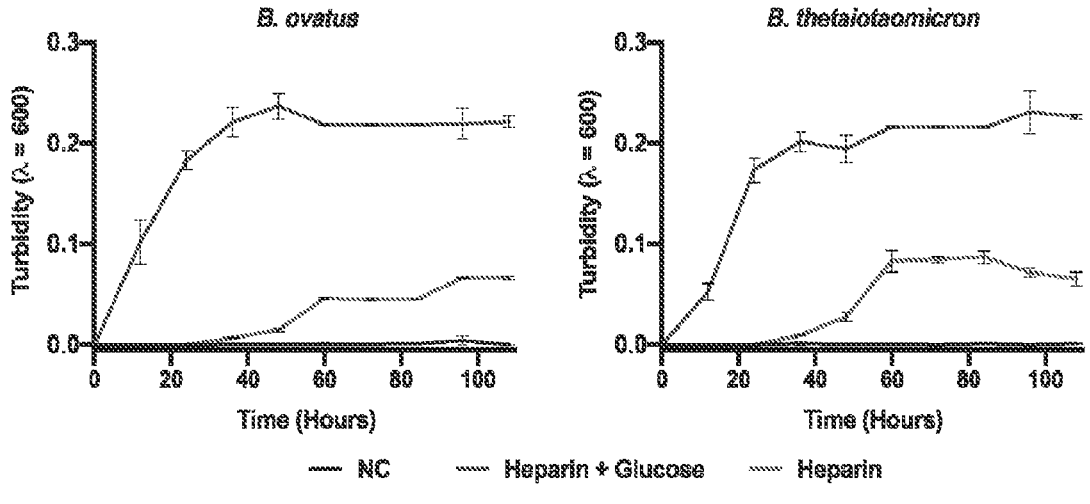
FIGURE 3A                                                    FIGURE 3B
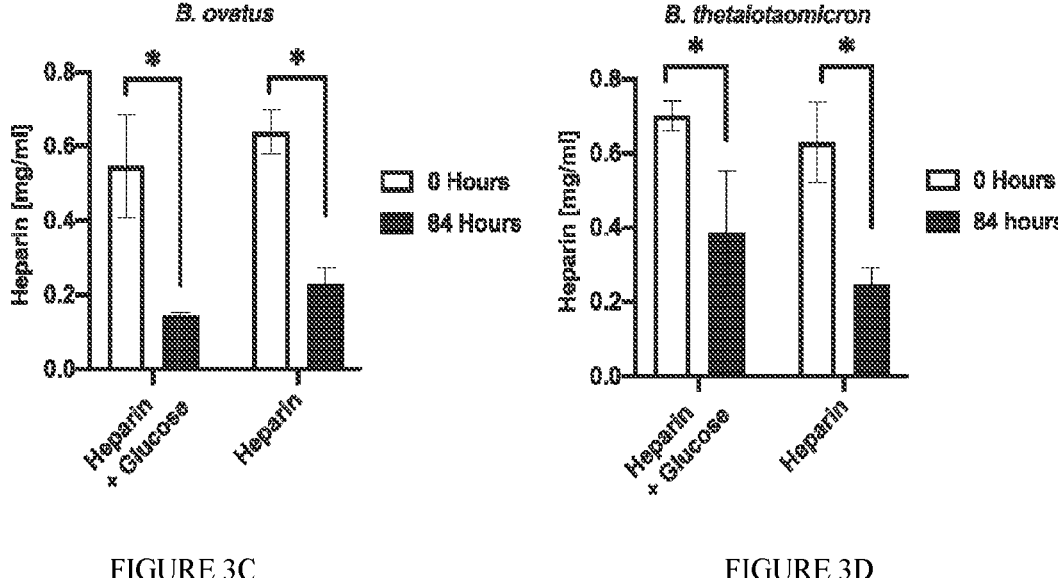
FIGURE 3C                                                    FIGURE 3D

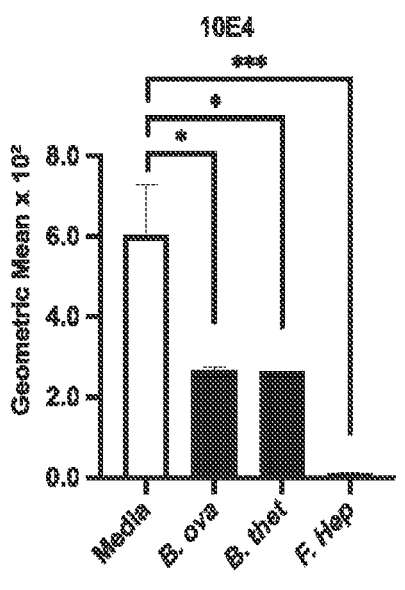
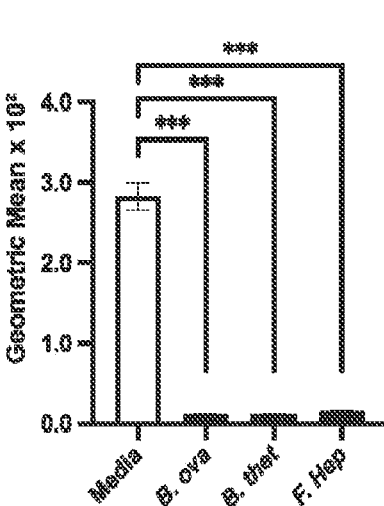
FIGURE 3E                                    FIGURE 3F
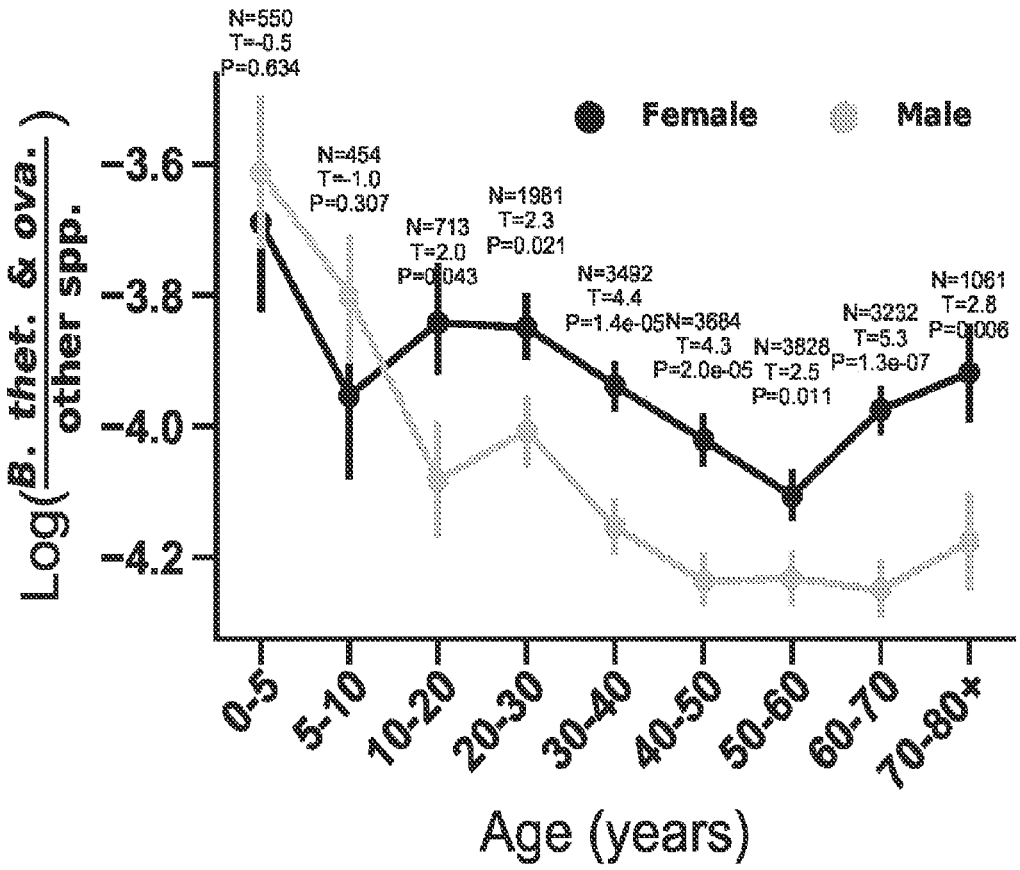
FIGURE 4

APPLICATION OF MICROBIAL GLYCOSIDASE AS AN ANTI-VIRAL THERAPEUTIC, PROGNOSTIC, AND DIAGNOSTIC

CROSS REFERENCE TO RELATED APPLICATIONS

This application is a U.S. National Phase Application of PCT Application No. PCT/US2021/046144, filed on Aug. 16, 2021, which claims priority benefit of U.S. Provisional Application No. 63/066,428, filed Aug. 17, 2020, the entire contents of which are incorporated herein by reference.

GOVERNMENT SPONSORSHIP

This invention was made with government support under Grant Nos. 1DP1AT010885 and HL131474 awarded by the National Institutes of Health, Grant Nos. 2038509 and 2031989 awarded by the National Science Foundation, Grant No. 1P30DK120515 awarded by the National Institute of Diabetes and Digestive and Kidney Diseases, and Grant No. R35GM119850 awarded by the National Institute of General Medical Sciences. The government has certain rights in the invention.

TECHNICAL FIELD

The present invention relates to an application of microbial glycosidase or sulfatase as a therapeutic anti-viral treatment.

BACKGROUND

All living cells are coated with a dense forest of glycans and glycoconjugates called the glycocalyx. Many viral pathogens have evolved mechanisms to attach to host glycans in order to bind to tissues and pass through the glycocalyx to engage protein receptors in the plasma membrane required for cell entry (Cagno et al., 2019). Of these, severe acute respiratory syndrome coronavirus (SARS-CoV) (Lang et al., 2011), dengue (Chen et al., 1997), human papillomavirus (Giroglou et al., 2001), hepatitis B (Schulze et al., 2007), herpes simplex virus (Spear et al., 1992), human immunodeficiency virus (Connell and Lortat-Jacob, 2013), and others, target heparan sulfate (HS), a highly negatively charged linear polysaccharide present on the surface of all mammalian cells (Esko and Selleck, 2002). Infection by SARS-CoV-2, the causative agent of COVID-19, can be blocked with the HS derivative heparin (Kim et al., 2020; Mycroft-West et al., 2020; Clausen and Sandoval et al., 2020). SARS-CoV-2 attachment and infection requires binding to both HS and angiotensin converting enzyme 2 (ACE2) via distinct regions of the receptor binding domain (RBD) (Clausen and Sandoval et al., 2020). Reducing the interaction between the SARS-CoV-2 spike protein and host-cell HS is therefore an attractive approach to reduce viral docking and subsequent infection.

Several bacterial taxa produce enzymes that modify specific classes of the glycosaminoglycan (GAG) family, including HS, and much of GAG research has been advanced using purified bacterial enzymes (Linhardt et al., 1986). Polysaccharide utilization loci (PUL) are co-localized and co-regulated genes responsible for complex carbohydrate detection and degradation in bacteria (Grondin et al. 2017). PULs have been annotated in *Bacteroides thetaiotaomicron* (human gut isolate; Cartmell et al., 2017; Ndeh et al., 2020; Ulmer et al., 2014) and *Flavobacterium heparinum* (soil isolate; Galliher et al., 1981). These PULs allow the bacteria to degrade and catabolize many complex carbohydrates including HS. The interplay of bacterial and viral utilization of host glycocalyx GAGs provides a mechanism for transkingdom interaction (Pfeiffer and Virgin, 2016) through modulation of pathogen adhesion spanning the eukaryotic host, bacteria in the microbiome, and viruses such as SARS-CoV-2. Removal of cell-surface HS via heparin lyase (HSase, heparinase) purified from *F. heparinum* effectively eliminates SARS-CoV-2 virus infection and spike protein binding (Clausen and Sandoval et al., 2020).

SUMMARY OF THE INVENTION

The present invention discloses the relationship between SARS-CoV-2 susceptibility and the capacity of the human microbiome to catabolize heparan sulfate (HS), a critical host factor involved in mediating SARS-CoV-2 infection. HS-modifying bacterial species *Bacteroides thetaiotaomicron* and *Bacteroides ovatus* are reduced in patients with COVID-19. Evidence shows that common commensal bacteria have the capacity to prevent SARS-CoV-2 spike protein binding by degrading host HS. These results suggest that differences in human microbiome composition influence SARS-CoV-2 and other viruses infectivity.

In embodiments, the invention provides a method of preventing or treating a viral infection in a subject comprising administering to a subject in need thereof an effective amount of a composition comprising a glycosidase or a sulfatase effective to degrade a glycan to inhibit viral infection. In embodiments, the invention provides that the glycan is heparan sulfate. In embodiments, the invention provides that the glycosidase breaks a glycosidic bond between sugars or a sugar and an aglycone to degrade the glycan. In embodiments, the invention provides that the sulfatase hydrolyzes a sulfate ester to degrade the glycan.

In embodiments, the invention provides that the glycosidase or the sulfatase is produced by a microbe. In embodiments, the invention provides that the glycosidase producing microbe is administered to the subject. In embodiments, the invention provides that the microbe is *B. ovatus* or *B. thetaiotaomicron*. In embodiments, the invention provides that the glycosidase or sulfatase is obtained from supernatant of a culture of *B. ovatus* or *B. thetaiotaomicron* or *Flavobacterium heparinum*. In embodiments, the invention provides that the glycosidase or the sulfatase is produced by a microbe genetically engineered to express the glycosidase or the sulfatase. In embodiments, the invention provides that the microbe genetically engineered to produce glycosidase or sulfatase administered to the subject is an *Escherichia coli* Nissle (EcN).

In embodiments, the invention provides that the glycosidase is heparin lyase. In embodiments, the invention provides that the sulfatase is N-acetylglucosamine-6-O-sulfatase or iduronate-2-O-sulfatase.

In embodiments, the invention provides pharmaceutical compositions comprising the glycosidase or the sulfatase, or the genetically engineered microbe described above, and a pharmaceutically acceptable carrier.

In embodiments, the invention provides a method of diagnosing a viral infection in a subject comprising detecting a decrease in amounts of glycosidase or sulfatase, or B. *ovatus* or B. *thetaiotaomicron*, in a biological sample from the subject, as compared to an earlier taken biological sample from the subject, or as compared to amounts of glycosidase or sulfatase, or *B. ovatus* or *B. thetaiotaomicron*, in a biological sample from a control subject.

In embodiments, the invention provides a method of prognosing a viral infection in a subject comprising detecting a decrease in amounts of glycosidase or sulfatase, or *B. ovatus* or *B. thetaiotaomicron*, in a biological sample from the subject, as compared to an earlier taken biological sample from the subject, or as compared to amounts of glycosidase or sulfatase, or *B. ovatus* or *B. thetaiotaomicron*, in a biological sample from a control subject.

In embodiments, the invention provides a method of determining susceptibility of a subject to a viral infection comprising detecting a lower amount of glycosidase or sulfatase, or *B. ovatus* or *B. thetaiotaomicron* in a biological sample from the subject, as compared to amounts of glycosidase or sulfatase, or *B. ovatus* or *B. thetaiotaomicron*, in a biological sample from a control subject.

In embodiments, the invention provides that the virus is SARS-CoV-2, causing COVID-19.

In embodiments, the invention provides a method of identifying a glycosidase or sulfatase, or a microbe associated with increased susceptibility to viral infection in a subject, comprising determining a decrease in amounts of a glycosidase or sulfatase, or *B. ovatus* or *B. thetaiotaomicron*, in a biological sample from a subject infected with a virus, as compared to amounts of the glycosidase or sulfatase, or *B. ovatus* or *B. thetaiotaomicron*, in a biological sample from a control subject not having the viral infection. Such identifications can be achieved using the methodologies described herein.

BRIEF DESCRIPTION OF THE DRAWINGS

FIGS. 3A-3F show HS-modifying bacteria degrade HS and reduce SARS-CoV-2 spike protein binding when applied to human lung cells. Growth of *Bacteroides ovatus* (FIG. 3A) and *Bacteroides thetaiotaomicron* (FIG. 3B) measured by optical density (y-axis) across time from inoculation (x-axis) in minimal media (black; negative control NC), minimal media with 22 mM glucose and 100 µM heparin (blue), or minimal media with 100 µM heparin (red). Comparison of heparin concentration (y-axis; mg/ml) before inoculation (white; zero hours) and at stationary phase (gray; 84 hours) for *B. ovatus* (FIG. 3C) and *B. thetaiotaomicron* (FIG. 3D). Geometric mean of FACS count data (y-axis) of H1299 cells stained with the HS antibody 10E4 (FIG. 3E) or incubated with biotinylated SARS-CoV-2 spike protein (FIG. 3F) when untreated (NC), or incubated with culture media negative control (Media), cell-free supernatant of *B. ovatus* (*B. ova*) or *B. thetaiotaomicron* (*B. thet.*) or purified HSase from *Flavobacterium heparinum* (*F. hep.*). Presented p-values are from unpaired t-test statistics (p>0.05 [n.s., not significant], p>0.05 [*], p≤0.01 [], p≤0.001 [*]).

FIG. 4 shows HS-modifying bacteria are depleted with host age and sex. The log-ratio of HS-modifying species *B. ovatus* and *B. thetaiotaomicron* relative to all others (y-axes) in the AGP fecal dataset compared over host age (x-axes). Log-ratios are colored by participant sex being female (black) and male (gray). All log-ratio plots annotated by the number of subjects at that time point. Error bars represent the standard error of the mean. Presented p-values and test statistics are from unpaired two-tailed t-test evaluated on each host age group between host sex.

DETAILED DESCRIPTION

Figure 1A:
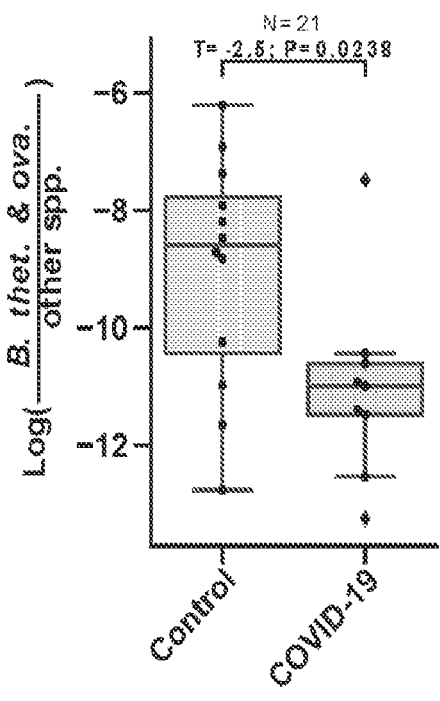
FIGS. 1A-1C show bacteria species encoding heparan sulfate lyase (HSase) are depleted in COVID patients compared to controls. BALF RNA-seq data from healthy subjects (control) and COVID-19 patients (COVID) (x-axes) compared by log-ratios (y-axes) of HS-modifying species *Bacteroides ovatus* and *Bacteroides thetaiotaomicron* relative to all other species (FIG. 1A) HSase relative to housekeeping set (FIG. 1B), and N-acetylglucosamine-6-O-sulfatase relative to housekeeping set (FIG. 1C). Significance was evaluated by a t-test and error bars represent the standard error of the mean. Presented p-values are from unpaired two-tailed t-test.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{th}$ ed., (Pharmaceutical Press and Philadelphia College of Pharmacy at University of the Sciences 2012).

In embodiments, the invention provides a method of preventing or treating a viral infection in a subject comprising administering to a subject in need thereof an effective amount of a composition comprising a glycosidase (or glycoside hydrolase) or a sulfatase effective to degrade a glycan to inhibit viral infection. In embodiments, the invention provides that the glycan is heparan sulfate. In embodiments, the invention provides that the glycosidase breaks a glycosidic bond between sugars, or a sugar and an aglycone, to degrade the glycan. In embodiments, the invention provides that the sulfatase hydrolyzes a sulfate ester to degrade the glycan.

In embodiments, the invention provides that the glycosidase or the sulfatase is produced by a microbe. In embodiments, the invention provides that the glycosidase producing microbe is administered to the subject. In embodiments, the invention provides that the microbe is *B. ovatus* or *B. thetaiotaomicron*. In embodiments, the invention provides that the glycosidase or sulfatase is obtained from supernatant of a culture of *B. ovatus* or *B. thetaiotaomicron* or *Flavobacterium heparinum*. In embodiments, the invention provides that the glycosidase or the sulfatase is produced by a microbe genetically engineered to express the glycosidase or the sulfatase. In embodiments, the invention provides that the microbe genetically engineered to produce glycosidase or sulfatase administered to the subject is an *Escherichia coli* Nissle (EcN).

In embodiments, the invention provides that the glycosidase is heparin lyase. In embodiments, the invention provides that the sulfatase is N-acetylglucosamine-6-O-sulfatase or iduronate-2-O-sulfatase.

In embodiments, the invention provides pharmaceutical compositions comprising the glycosidase or the sulfatase, or the genetically engineered microbe described above, and a pharmaceutically acceptable carrier.

In embodiments, the invention provides a method of diagnosing a viral infection in a subject comprising detecting a decrease in amounts of glycosidase or sulfatase, or *B. ovatus* or *B. thetaiotaomicron*, in a biological sample from the subject, as compared to an earlier taken biological sample from the subject, or as compared to amounts of glycosidase or sulfatase, or *B. ovatus* or *B. thetaiotaomicron*, in a biological sample from a control subject.

In embodiments, the invention provides a method of prognosing a viral infection in a subject comprising detecting a decrease in amounts of glycosidase or sulfatase, or *B. ovatus* or *B. thetaiotaomicron*, in a biological sample from the subject, as compared to an earlier taken biological sample from the subject, or as compared to amounts of glycosidase or sulfatase, or *B. ovatus* or *B. thetaiotaomicron*, in a biological sample from a control subject.

In embodiments, the invention provides a method of determining susceptibility of a subject to a viral infection comprising detecting a lower amount of glycosidase or sulfatase, or *B. ovatus* or *B. thetaiotaomicron* in a biological sample from the subject, as compared to amounts of glycosidase or sulfatase, or *B. ovatus* or *B. thetaiotaomicron*, in a biological sample from a control subject.

In embodiments, the invention provides that the virus is SARS-CoV-2, causing COVID-19.

In embodiments, the invention provides a method of identifying a glycosidase or sulfatase, or a microbe associated with increased susceptibility to viral infection in a subject, comprising determining a decrease in amounts of a glycosidase or sulfatase, or *B. ovatus* or *B. thetaiotaomicron*, in a biological sample from a subject infected with a virus, as compared to amounts of the glycosidase or sulfatase, or *B. ovatus* or *B. thetaiotaomicron*, in a biological sample from a control subject not having the viral infection. Such identifications can be achieved using the methodologies described herein.

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a fusion protein, a pharmaceutical composition, and/or a method that "comprises" a list of elements (e.g., components, features, or steps) is not necessarily limited to only those elements (or components or steps), but may include other elements (or components or steps) not expressly listed or inherent to the fusion protein, pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a fusion protein, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated.

As used herein the term "pharmaceutical composition" refers to pharmaceutically acceptable compositions, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

Sterile compositions are within the present disclosure, including compositions that are in accord with national and local regulations governing such compositions. Pharmaceutical compositions and a glycosidase, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. A glycosidase, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, a glycosidase or a sulfatase, alone or in combination with another active ingredient, may be provided in a solid form, such as a tablet or capsule, or as a solution, emulsion, or suspension. To prepare the oral compositions, a glycosidase or a sulfatase, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and diglycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, a glycosidase, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, a glycosidase or a sulfatase, alone or in combination with other active ingredient(s), may be administered using, for example, a spray formulation also containing a suitable carrier.

For topical applications, a glycosidase or a sulfatase, alone or in combination with other active ingredient(s), are preferably formulated as creams or ointments or a similar vehicle suitable for topical administration. For topical administration, a glycosidase or a sulfatase, alone or in combination with other active ingredient(s), may be mixed with a pharmaceutical carrier at a concentration of about 0.1% to about 10% of drug to vehicle. Another mode of administering a glycosidase or a sulfatase, alone or in combination with other active ingredient(s), may utilize a patch formulation to effect transdermal delivery.

One of ordinary skill in the art may modify the formulations within the teachings of the specification to provide numerous formulations for a particular route of administration. In particular, a glycosidase or a sulfatase, alone or in combination with other active ingredient(s), may be modified to render them more soluble in water or other vehicle. It is also well within the ordinary skill of the art to modify the route of administration and dosage regimen of a particular glycosidase or a sulfatase, alone or in combination with other active ingredient(s), in order to manage the pharmacokinetics of the present compositions for maximum beneficial effect in a patient.

As used herein, "therapeutically effective amount" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

The term "antibody" as used herein encompasses monoclonal antibodies (including full length monoclonal antibodies), polyclonal antibodies, multi-specific antibodies (e.g., bi-specific antibodies), and antibody fragments so long as they exhibit the desired biological activity of binding to a target antigenic site and its isoforms of interest. The term "antibody fragments" comprise a portion of a full length antibody, generally the antigen binding or variable region thereof. The term "antibody" as used herein encompasses any antibodies derived from any species and resources, including but not limited to, human antibody, rat antibody, mouse antibody, rabbit antibody, and so on, and can be synthetically made or naturally-occurring.

A more complete understanding can be obtained by reference to the following specific examples which are provided herein for purposes of illustration only, and are not intended to limit the scope of the invention.

EXAMPLES

HS-Modifying Bacteria are Reduced in COVID-19 Patients

Figure 1B:
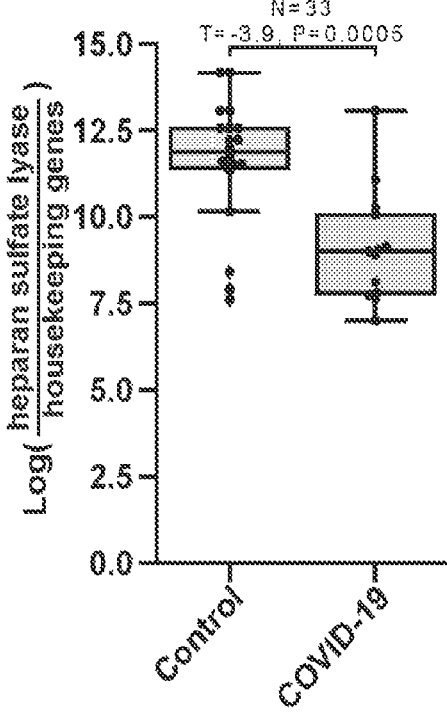
Figure 1C:
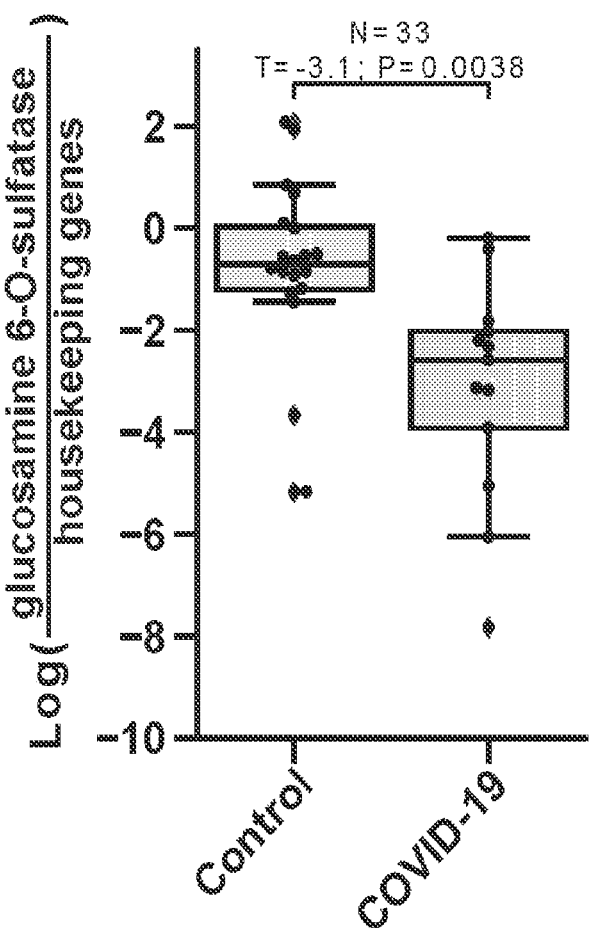
Figure 2A:
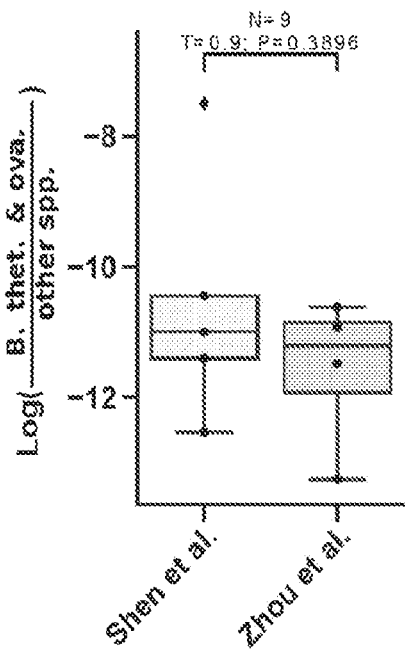
FIGS. 2A-2C show BALF RNA-seq data compared between studies. RNA-seq studies (x-axes) compared by log-ratios (y-axes) of HS-modifying species *Bacteroides ovatus* and *Bacteroides thetaiotaomicron* relative to all other species (FIG. 2A), HSase relative to housekeeping set (FIG. 2B), and N-acetylglucosamine-6-O-sulfatase relative to housekeeping set (FIG. 2C).
Figure 2B:
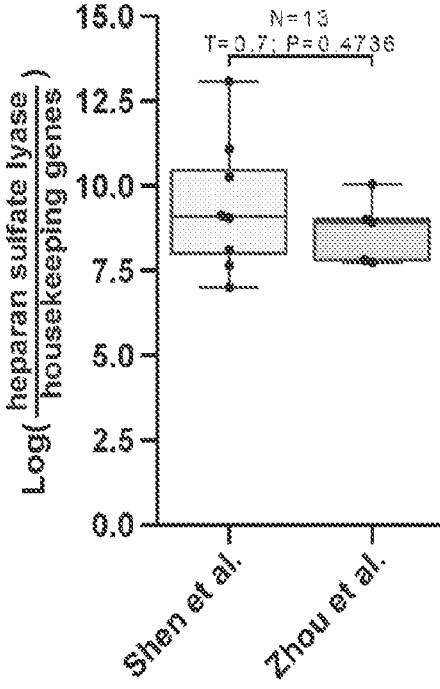
Figure 2C:
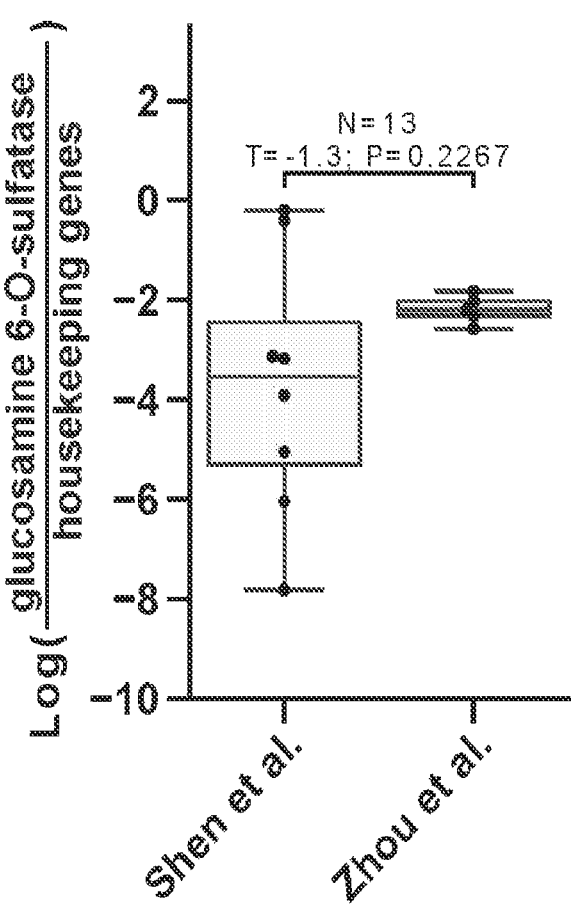
Figure 5:
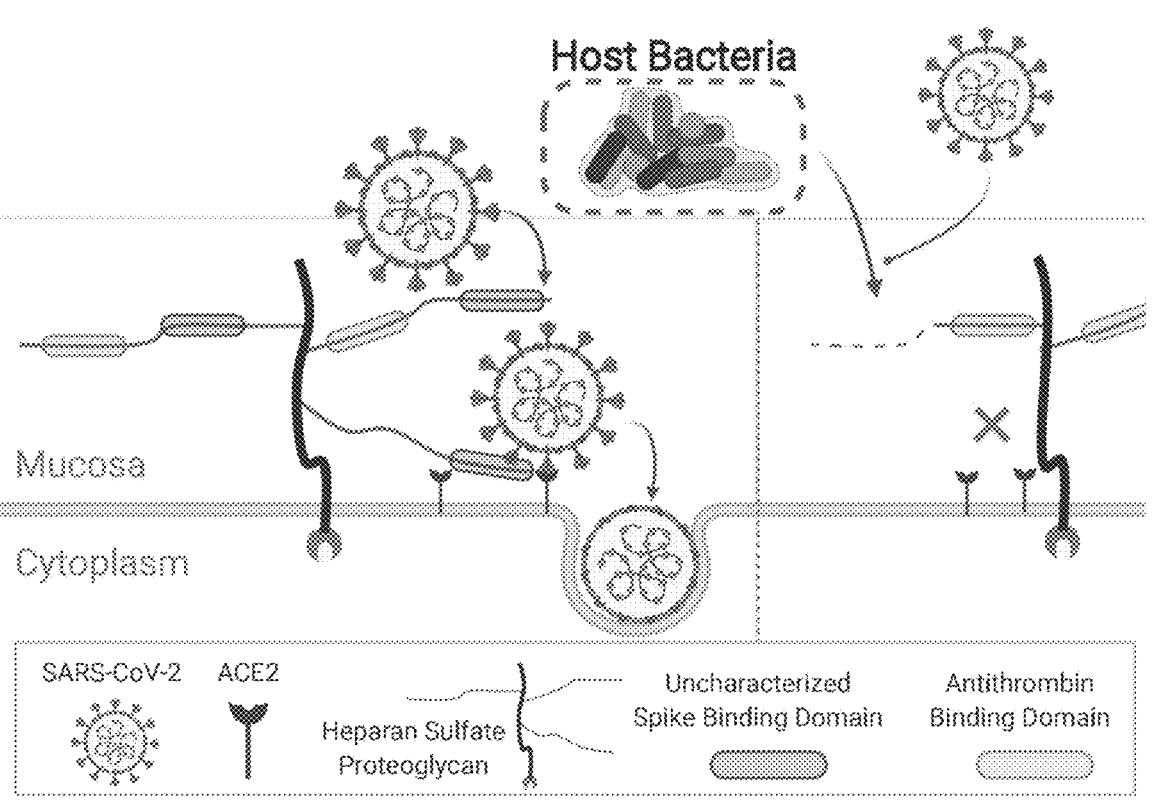
FIG. 5 shows a diagram of hypothesis for bacterial mediation of SARS-CoV-2 infection through heparan sulfate (HS). It is well known that host microbes groom the mucosa where they reside. Recent investigations have shown that HS, a major component of mucosal layers, is necessary for SARS-CoV-2 infection. In this study the impact of microbial modification of HS on viral attachment was examined.
Figure 6:
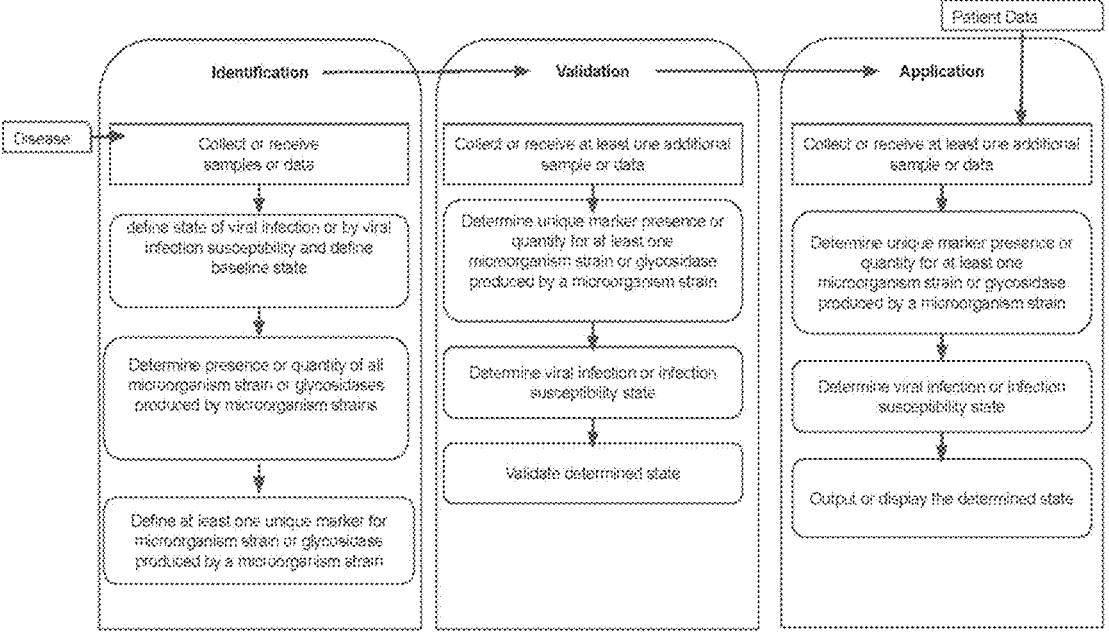
FIG. 6 shows a schematic of the methods for identification, validation and application of embodiments of the present invention.

Based on the prevalence of bacteria that can potentially catabolize HS such as *Bacteroides* spp., it was hypothesized that their presence within the microbiome might naturally limit HS-binding sites for SARS-CoV-2 and that the prevalence of bacteria encoding these genes might associate negatively with COVID-19 susceptibility. To test this hypothesis, the prevalence of the HS-modifying bacteria *Bacteroides thetaiotaomicron* and *Bacteroides ovatus* in COVID-19 patient samples was explored. Human and SARS-CoV-2 reads were filtered out of previously published RNA-Seq datasets from 33 bronchoalveolar lavage fluid (BALF) samples from adult COVID-19 (n=13) and healthy control (n=20) subjects (Shen et al. 2019; Zhou et al. 2020) to obtain microbial reads (Poore et al., 2020). Gene expression from HS-modifying bacteria (N-strains numerator=239, denominator=1851) was decreased in COVID-19 compared to healthy control samples (FIG. 1A). Microbial RNA-Seq reads coding for heparin lyase (class I, II, & III) (FIG. 1B), and N-acetylglucosamine-6-O-sulfatase (FIG. 1C), both HS-modifying enzymes, were also reduced in COVID-19 patients compared to healthy controls. These differences were not explained by variation between the two datasets included (FIG. 2). These findings suggest that COVID-19 patients have altered lung microbiomes that may favor SARS-CoV-2 infection.

Common Human Gut Commensal Bacteria are Capable of Degrading HS

To provide more direct evidence for the hypothesis, in vitro experiments were conducted to test the catabolic capacity of human microbiome species to degrade HS. Axenic cultures of *B. ovatus* and *B. thetaiotaomicron*, highly prevalent human gut bacterial isolates known to catabolize HS (Cartmell et al., 2017), were grown on minimal medium in the presence of heparin (100 µM) with and without glucose (22 mM). Both species were able to grow with heparin as the sole carbon source and electron donor (FIG. 3A-3B). Furthermore, all cultures were verified to catabolize heparin in culture by comparing the concentration of heparin in the medium before and after stationary growth (FIG. 3C-3D). Cell-surface HS on H1299 human lung cells was reduced by 60% upon exposure to cell-free supernatants from mid-log phase cultures of *B. ovatus* or *B. thetaiotaomicron* compared to 100% reduction by purified heparin lyase from *Flavobacterium heparinum* (*F. hep.* HSase; IBEX pharmaceuticals), as measured by binding of the anti-HS monoclonal antibody 10E4 (FIG. 3E).

To determine the effect of bacterial HS modification on SARS-CoV-2 binding, H1299 human lung cells were treated with the supernatant of *Bacteroides* cultures or purified *F. hep.* HSase, and then incubated with biotinylated trimeric SARS-CoV-2 spike protein and assessed cell-surface binding by flow cytometry. Cells treated with *Bacteroides* culture supernatant caused a significant reduction (20-30 fold) in SARS-CoV-2 spike protein binding to cells incubated with *Bacteroides* culture supernatants compared to untreated H1299 cells (*B. ovatus* t-statistic=31.25, p-value=7.019× $10^{-5}$; *B. thetaiotaomicron* t-statistic=30.99, p-value=7.023× $10^{-5}$), similar to the reduction observed by pre-treatment with purified Hsase (t-statistic=23.89, p-value=7.59× $10^{-5}$) (FIG. 3F).

HS Lyases Reduce SARS-CoV-2 S Protein Binding

Figure 7:
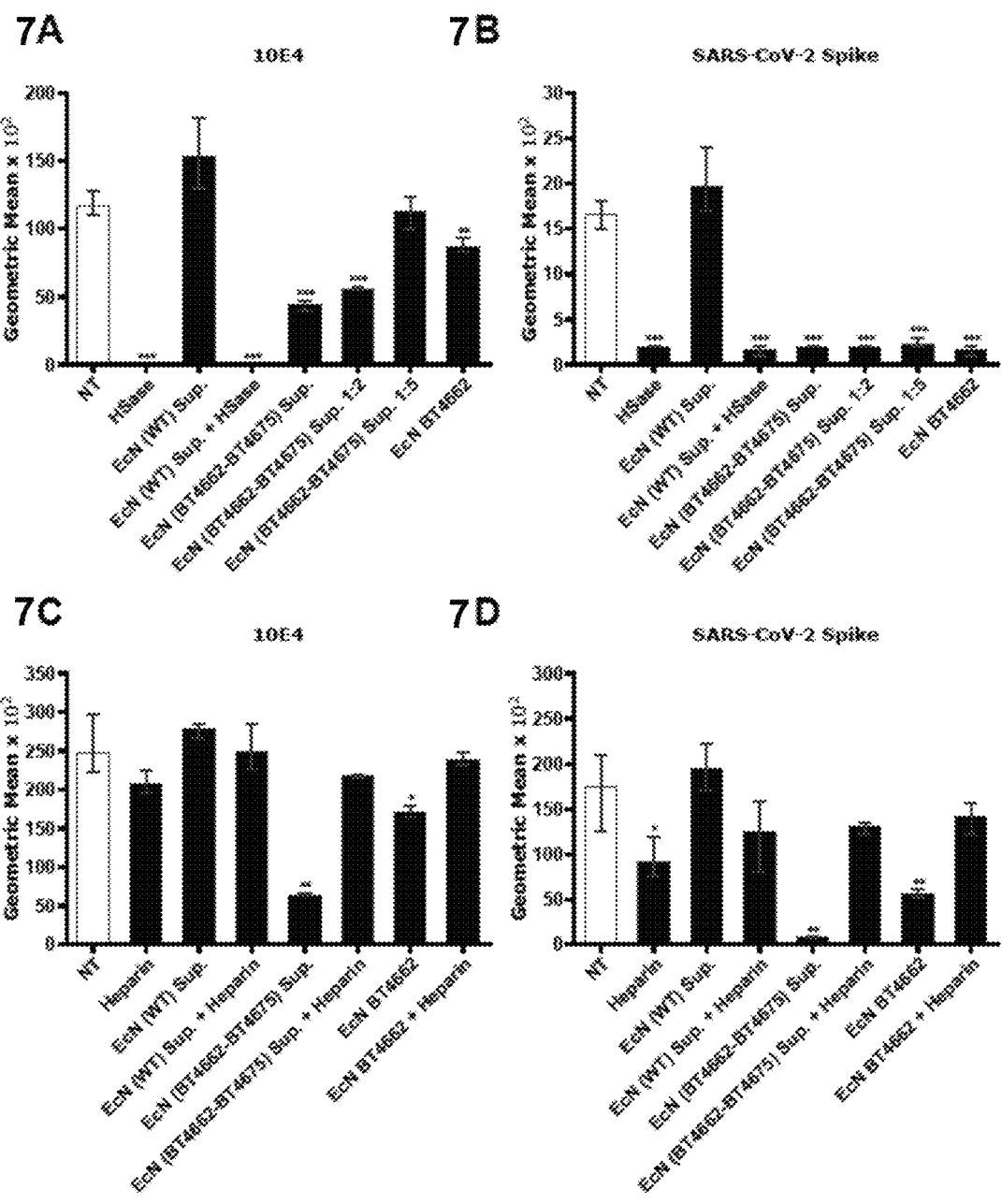
FIG. 7 shows geometric mean of FACS count data of EcN endo-lyase data. Geometric mean of FACS count data (y-axis) of cultured human cells stained with the HS antibody 10E4 (A&C) or incubated with biotinylated SARS-CoV-2 spike protein (B&E), with no treatment (NT) or treated with purified HSase from *Flavobacterium heparinum* (*F. hep.*), supernatant from EcN wild type (WT) or EcN (BT4662-BT4675), or purified BT4662 with and without heparin rescue of HS and spike binding. Presented p-values are from unpaired t-test statistics w.r.t. NT (p≤0.05 [*], p≤0.01 [], p>0.001 [*]).

Next, human commensal bacterial endo-acting HS lyases were tested for the capacity to reduce SARS-CoV-2 S protein binding. Specifically, two endo-lyases sourced from *B. thet.*: BT4662 (polysaccharide Lyase family 12; PL12) a depolymerizing cell surface lyase that targets sulfate-poor HS and BT4675 (polysaccharide Lyase family 13; PL13) capable of degrading sulfate-rich HS (Cartmell and Lowe et al., 2017). Both enzymes were co-expressed in the safe and widely used probiotic *Escherichia coli* strain Nissle 1917 (EcN) with unique purification tags. The human cell line A549 was treated with culture supernatant from both the EcN wild type (WT) and engineered EcN (BT4662-BT4675) at three dilutions, in parallel to samples treated with the purified endo-lyases BT4662, and a positive control of purified *F. hep.* HSase (IBEX pharmaceuticals). As demonstrated previously, the positive control, *F. hep.* HSase eliminated both host-cell HS as detected by 10E4 staining (t-statistic=−1394.6, p-value=1.58×10−12) and binding of recombinant SARS-CoV-2 S protein (t-statistic=−95.26, p-value=7.28×10−8). EcN (WT) culture supernatant produced no significant difference in host cell-surface HS or SARS-CoV-2 S protein binding alone and did not interfere with significant reductions in both HS and S binding when combined with *F. hep.* HSase (10E4, t-statistic=−4602.01, p-value=1.33×10−14; SARS-CoV-2 S, t-statistic=−82.77, p-value=1.28×10−7). EcN (BT4662-BT4675) culture supernatant significantly decreased host-cell surface HS except at a dilution of 1:5 (1:1, t-statistic=−22.71, p-value=2.23×10−5; 1:2, t-statistic=−22.38, p-value=2.35×10−5; 1:5, t-statistic=−0.45, p-value=0.67) and significantly reduced SARS-CoV-2 S binding at all dilutions (1:1, t-statistic=−59.83, p-value=4.67×10−7; 1:2, t-statistic=−49.84, p-value=9.69× 10−7; 1:5, t-statistic=−68.11, p-value=2.78×10−7). Similarly, purified BT4662 alone ablated SARS-CoV-2 S binding (t-statistic=−80.71, p-value=1.41×10−7). Interestingly, EcN (BT4662-BT4675) supernatant and purified BT4662 largely eliminated SARS-CoV-2 S binding without full elimination of host-cell surface HS (FIG. 7). Finally, the enzymatic activity on HS of EcN (BT4662-BT4675) culture supernatant and purified EcN BT4662 was tested in the presence of 100 µg/mL heparin as a competitive substrate, which was then washed away prior to binding of 10E4 or S protein. Both HS degradation and SARS-CoV-2 S protein binding were rescued by inclusion of heparin in the pre-incubation medium (FIG. 7). These findings demonstrate the ability of EcN (BT4662-BT4675), encoded with human gut sourced microbial HS degradation capacity, to reduce HS presentation and SARS-CoV-2 S protein binding.

Bacteria with Capacity for HS Modification Decrease with Age

To determine if HS-modifying bacteria could reduce the risk of SARS-CoV-2 infection, their prevalence across age and sex, two established COVID-19 risk-factors, was explored. Strong age and sex disparities in SARS-CoV-2 infection susceptibility has been reported across numerous populations, with adults twice as likely to be infected as those under the age of 20 (Davies et al., 2020) and men having higher risk than females (Williamson et al., 2020). Microbial communities age naturally and predictably with their human hosts in a sex-dependent manner (McDonald et al., 2018; de la Cuesta-Zuluaga et al., 2019; Claesson et al., 2011; Huang et al., 2020; Koenig et al., 2011), suggesting that aging and sex may be associated with a reduction in HS-modifying bacteria.

To test this hypothesis, the prevalence of HS-modifying bacteria across age for both men and women in the American Gut Project (AGP), a citizen-science dataset with participants ranging in age from 1-80 years (McDonald et al., 2018), was measured. A mapping the Web of Life (WoL) microbial genomes (Zhu et al., 2019) 16S rRNA gene amplicon sequence variants (ASVs). An age and sex-dependent decrease in HS-modifying bacteria *Bacteroides thetaiotaomicron* and *Bacteroides ovatus* was observed (FIG. 4). This, in combination with the COVID-19 BALF patient results, indicates that the abundance of HS-modifying bacteria may provide a measure of susceptibility.

The present disclosure provides evidence for a role of the human microbiome in mediating SARS-CoV-2 infectivity via modification of the host glycocalyx. HS-modifying bacteria, identified in the human gut microbiome, were depleted in BALF of COVID-19 patients. Although no protective mechanism has been demonstrated yet, HS-modifying *Bacteroides* strains have previously been shown to be more frequent in healthy controls compared to COVID-19 patients (Trottein and Sokol, 2020; Zuo et al., 2020). *B. ovatus* and *B. thetaiotaomicron* can catabolize cell-surface HS and block SARS-CoV-2 S protein binding. Finally, it was experimentally shown that *B. ovatus* and *B. thetaiotaomicron* can catabolize cell-surface HS and block SARS-CoV-2 S protein binding.

Human-associated microbes, including the *Bacteroides* species tested here, may alter viral infectivity in other ways. For example, ACE2, the plasma membrane receptor necessary for viral uptake, was downregulated in germ-free mice mono-colonized by *B. ovatus* or *B. thetaiotaomicron* (Geva-Zatorsky et al., 2017). *Bacteroides* species, including *B. ovatus* and *B. thetaiotaomicron*, have previously been found to be negatively associated with host age (Galkin et al., 2020). Recent work has demonstrated that the receptor binding domain of SARS-CoV-2, unlike previous SARS-like coronaviruses, must be pre-activated by the proprotein convertase furin to effectively bind ACE2 (Walls et al., 2020, Hoffman 2020). Certain bacteria can also produce furin-like proteases and may provide another layer of regulation on top of host-produced furin proteases (Pavlova 2019). More generally, the effect of the microbiome on immune system development and decay has been widely documented (Thaiss et al., 2016), and may also influence an individual's susceptibility to COVID-19.

Positioned at the cell-environment interface, glycosaminoglycans (GAG), like HS, play critical roles in intercellular and host-pathogen interactions ranging from peptide exchange to migration (Weiss et al., 2017). Removal of critical molecules like HS may mitigate SARS-CoV-2 infection, but their depletion could also result in the loss of its endogenous function, for example in signaling reactions and tissue repair processes. Further studies are required to determine the target sulfation pattern for SARS-CoV-2 binding, but the resent results suggest that N-acetylglucosamine-6-O-sulfatase is decreased in the microbial populations present in COVID-19 patients. Activation of host 6-O-sulfotransferases decreased spike protein binding and dramatically reduced SARS-CoV-2 infection in tissue culture (Clausen and Sandoval et al., 2020), suggesting that 6-O-sulfation of HS may provide a more specific target to disrupt the SARS-CoV-2/HS interaction without broad degradation of host cell surface or extracellular matrix HS. This report provides evidence for the role of glycocalyx-microbiota interactions as a novel competitive mechanism in the fight against SARS-CoV-2 and other viruses.

Methods

Abundance and Expression by Log-Ratios

Differential abundance or expression of HS-modifying bacteria was determined by the log-ratio of mapped reads for each sample of those bacteria. Functional gene abundance or expression was determined with a log-ratio of the total mapped reads to that gene relative to the sum of counts of total mapped reads from a set of housekeeping genes in each sample. The housekeeping gene set is comprised of all bacterial nucleotide sequences for the genes atpD, dnaJ, gyrA, gyrB, infB, pheS, proC, rpoA, rpoB, and rpoD obtained from RefSeq (Pruitt et al., 2007). Significance between groups of log-ratios was determined with an unpaired t-test though SciPy (Virtanen et al., 2020).

COVID-19 RNA-Seq Dataset

Previously, COVID-19 metatranscriptomes have been analyzed for microbial taxonomy and function (Shen et al. 2020; Zhou et al. 2020; Haiminen et al. 2020). RNA-Seq data from two separate studies on SARS-CoV-2 infected patients (Shen et al., 2020; Zhou et al., 2020) were downloaded from the National Genomics Data Center (Project Accession PRJCA002202) and NCBI's Sequence Read Archive (Project Accession PRJNA605983). Human and SARS-CoV-2 reads were filtered out by aligning reads to the human genome (Genome Reference Consortium Human Build 38) (Church et al., 2011; Schneider et al., 2017) and SARS-CoV-2 genome using Bowtie2 (Langmead and Salzberg, 2012) with the fast-local parameter set, following the protocol described by Poore et al. In the case of paired-end reads, forward and reverse reads files were treated as unpaired. Reads were aligned to the Web of Life database of 10,575 bacterial and archaeal genomes using Shogun (Hillmann et al., 2018) in the Bowtie2 alignment mode. Alignments were summarized into taxonomic profiles at the phylum, genus, and species level using the classify function in the Web of Life (Zhu et al., 2019).

Mapping of WoL to AGP 16S ASVs

To reconcile the evolutionary relationships among 16S rRNA gene sequencing amplicon sequence variants (ASV) and shotgun metagenomic data, the ASVs were mapped to the "Web of Life" (WoL) (Zhu et al., 2019) reference phylogeny of bacterial and archaeal genomes. First, 16S rRNA genes were annotated from each of the 10,575 genomes included in the phylogeny using RNAmmer 1.2 (Lagesen et al., 2007), using domain-specific models (bacteria and archaea, respectively). Second, filtered 150 bp length 16S V4 American Gut Project (McDonald et al., 2018) ASVs (n=15,486) were aligned to the WoL 16S rRNA genes using BLASTn 2.7.1+ (Altschul et al., 1990), with an e-value threshold of 1e-5 and up to 100 target sequences per query. Top hits with identical bit scores of each query were retained and subjected to taxonomic classification. At each designated rank, taxonomic assignments of all top hits were recorded. For feature table generation, the hits were counted and normalized by the total number of hits. As an example, assuming one ASV aligned equally well to five reference full-length 16S sequences, and they belong to genus A (two sequences) and genus B (three sequences), then the two genera were counted as 2/5 (A) and 3/5 (B), respectively. Per-query counts were summed across each AGP sample and rounded to integers.

Cultivation of *Bacteroides* Strains

*Bacteroides thetaiotaomicron* and *Bacteroides ovatus* were cultured in 50 mL anaerobic brain heart infusion (BHI) medium with overnight incubation at 37° C. in an anaerobic serum bottle. The next day, 1 mL of cells from the BHI culture were washed in anaerobic PBS and were passed into 15 mL of minimal medium containing no carbon sources or electron donors other than glucose (22 mM final) and/or heparin (1 mg/mL final). Growth on the minimal medium was measured by optical density at 600 nm every 12 hr. Aliquots of 3 mL of culture were taken before inoculation, immediately after inoculation, at mid-log phase (24 hr), and in stationary phase (45 hr). Heparin degradation in culture was measured through a Blyscan glycosaminoglycan assay (Biocolor Ltd., Carrickfergus, Northern Ireland) using 100 µL of time 0- and 45-hr culture media. All cultivation and HS-modification experiments were conducted in triplicate.

To verify strain taxonomy a 1 mL aliquot of each culture was extracted using PowerFecal DNA Isolation Kit (MoBio cat. 12830). Extracted DNA was quantified via Qubit™ dsDNA HS Assay (Thermo Fisher Scientific), and 5 ng of input DNA was used in a 1:10 miniaturized Kapa HyperPlus protocol (Sanders et al., 2019). The pooled library was sequenced as a paired-end 150-cycle run on an Illumina NovaSeq at the UCSD IGM Genomics Center. Resulting sequences were adapter trimmed using Trimmomatic v0.39 (Bolger et al., 2014) and human read filtered with Bowtie2 (Langmead and Salzberg, 2012). Paired-end reads were merged using Flash v1.2.11 (Magoč and Salzberg, 2011). Each axenic sample was assembled through SPAdes (Bankevich et al., 2012) and verified through average nucleotide identity (Lee et al., 2016) of greater than 99% between the assembled genome and the putative type-strain genome obtained from NCBI (Pruitt et al., 2007).

SARS-CoV-2 Spike Protein Production

Recombinant SARS-CoV-2 spike protein encoding residues 1-1138 (Wuhan-Hu-1; GenBank: MN908947.3) with proline substitutions at amino acids positions 986 and 987 and a "GSAS" substitution at the furin cleavage site (amino acids 682-682), was produced in ExpiCHO cells by transfection of 6×106 cells/ml at 37° C. with 0.8 µg/ml of plasmid DNA using the ExpiCHO expression system transfection kit in ExpiCHO Expression Medium (ThermoFisher). One day later the cells were refed, then incubated at 32° C. for 11 days. The conditioned medium was mixed with cOmplete EDTA-free Protease Inhibitor (Roche). The recombinant protein was purified by chromatography on a Ni2+ Sepharose 6 Fast Flow column (1 ml, GE LifeSciences). Samples were loaded in ExpiCHO Expression Medium supplemented with 30 mM imidazole, washed in a 20 mM Tris-Cl buffer (pH 7.4) containing 30 mM imidazole and 0.5 M NaCl. The recombinant protein was eluted with buffer containing 0.5 M NaCl and 0.3 M imidazole. The protein was further purified by size exclusion chromatography (HiLoad 16/60 Superdex 200, prep grade. GE LifeSciences) in 25 mM HEPES buffer (pH 7.5) containing 0.3 M NaCl.

Biotinylation

For binding studies, recombinant SARS-CoV-2 spike protein was conjugated with EZ-LINK Sulfo-NHS-Biotin (1:3 molar ratio; Thermo Fisher) in Dulbecco's PBS at room temperature for 30 min. Glycine (0.1 M) was added to quench the reaction and the buffer was exchanged for PBS using a Zeba spin column (Thermo Fisher).

SARS-CoV-2 Spike Binding Experiments

NCI-H1299 or A549 from the American Type Culture Collection were grown in RPMI medium containing 10% FBS and 100 U/mL penicillin and 100 µg/mL streptomycin sulfate under an atmosphere of 5% $CO_2$ and 95% air. Cells at 50-80% confluence were lifted in 10 mM EDTA in PBS (Gibco) and washed in PBS containing 0.5% BSA. Cells were seeded into a 96 well plate at $10^5$ cells per well. The cells were then treated with a mix of 2.5 mU/mL *Flavobac-*

*terium heparinum* HSase II and 5 mU/mL *Flavobacterium heparinum* HSase III (IBEX Pharmaceuticals) in PBS containing 0.5% BSA (100 µL), 100 µL *Bacteroides ovatus* and *thetaiotaomicron* or *Escherichia coli* strain Nissle 1917 minimal media cell-free culture supernatant supplemented with 10% BSA), or purified sulfatase or lyase enzymes at the given concentration for 30 min at 37° C. The cells were washed twice in PBS containing 0.5% BSA. The cells were then stained with 202025 µg/mL biotinylated S protein (S1/S2) or 1:1000 Anti-HS (Clone F58-10E4) (Fisher Scientific, NC1183789) in PBS containing 0.5% BSA, for 30 min at 4° C. The cells were washed twice and then stained with Streptavidin-Cy5 (Thermo Fisher) at 1:1000 (S protein) or Anti-IgM-Alexa488 at 1:1000 (Anti-HS) in PBS containing 0.5% BSA, for 30 min at 4° C. The cells were washed twice and then analyzed using a FACSCanto instrument (BD bioscience). Data analysis was performed in FlowJo and statistical analyses were done in Prism 8.

Lyase Expression in *E. coli* Nissle 1917

Lyases BT4675 and BT4662 were amplified from the genome of *Bacteroides thetaiotaomicron*, and inserted into pRSF-Duet using Golden Gate Assembly. The resulting plasmid was transformed into *E. coli* Nissle 1917 via electroporation. For lyase expression, a starter culture of *E. coli* Nissle 1917 containing the lyase plasmid was grown overnight in LB media containing 50 µg/mL of kanamycin, and then used to inoculate 500 ml of the same media. Cells were grown until they reached optical density 0.1-0.2, induced with 1 mM IPTG, and incubated overnight at room temperature. Cells were pelleted by centrifugation at 5,000×g for 5 minutes, and the supernatant was removed for further experiments. The recombinant protein was purified by flowing over a Ni2+ Sepharose 6 Fast Flow column (1 ml, GE LifeSciences), and eluted with 0.3 M imidazole, 0.5 M NaCl, 25 mM HEPES pH7.5. Protein was concentrated and buffer exchanged using a PES Pierce™ Protein concentrators (Thermo).

Heparan Sulfate Modification Capability (Completeness and Capacity) Prediction for Discovery of Additional Therapeutic Microbes HS modification capacity in a microbial species can be predicted by a gene set in a metabolic task, i.e. a group of reactions necessary to transition between metabolites (Richelle et al., 2020) used to describe a complete pathway of HS modification. Pathways from the Kyoto Encyclopedia of Genes and Genomes (KEGG, ec00531, (Kanehisa et al., 2017)), in combination with literature annotation of these pathways for specific bacteria (Hobbs et al., 2018; Robb et al., 2017; Ndeh et al., 2017), can be used to identify reactions (enzyme commission (EC) numbers) associated with the modification task. Then CAZy, dbCAN, and CUPP (Barrett and Lange, 2019; Lombard et al., 2014; Yin et al., 2012; Zhang et al., 2018) can be used to map EC numbers to microbial genes associated with glycan modification.

For each microbe in the shotgun microbiome dataset, an estimated pathway "Completeness," a binary indication of the presence or absence of all genes in the task, and pathway "Capacity," a continuous indication of the magnitude of flux that could travel through the task can be predicted. Expression of genes associated with glycan catabolism were quantified by the total number of reads (total count) mapped between the HS-modification gene set and each sample shotgun dataset through Bowtie2. A pseudocount will be added to each count and log-transformed, log(count+1), to stabilize variance.

HS-catabolic completeness ($E_i$) for each organism, i, with gene, g, is an indication that all reactions in a task are represented in an organism. Specifically, for each reaction (EC) in the HS task, can be calculated by the sum the log-counts aligned to glycosylation-related genes within an organism associated with that EC. If the sum of log counts aligned to an EC exceeds a threshold, t, the EC can be marked as active in that organism. The threshold, t, can be set at a percentile of log-counts aligned to glycosylation-associated genes in the microbiome shotgun database. If all ECs in the HS task were active in an organism, the HS task is considered complete.

$$O_i = \forall_{EC \in Task}\ t < \sum_g^{EC} \log(read_g)$$

To quantify the HS-catabolic capacity ($A_i$) of each organism, i, with genes, g, the expression of all glycosylation-related genes within the catabolic task was analyzed. Adapted from metabolic task analysis (Richelle et al., 2018, 2019, 2020), the catabolic capacity of a microbe is a context-sensitive measure that accommodates rate-limiting or low-abundance enzymes and can therefore accommodate microbial gene transience. Activation of the glycan degrading metabolic task (Richelle et al., 2020), was calculated as the minimum EC activation; the maximum activation of genes performing the EC reaction within an organism. Log of total counts can be used to stabilize variance. The capacity is the minimum EC activation in a pathway where EC activation is the maximum gene activity score for each EC within a microbe. The log of total counts aligned to each gene in the microbiome dataset can be used for the gene activity score:

$$A_i = \min_{EC \in Task} \max_{g \in EC} \log(reads_g).$$

REFERENCES

1. Agelidis, A., and Shukla, D. (2020). Heparanase, Heparan Sulfate and Viral Infection. Adv. Exp. Med. Biol. 1221, 759-770.
2. Altschul, S. F., Gish, W., Miller, W., Myers, E. W., and Lipman, D. J. (1990). Basic local alignment search tool. J. Mol. Biol. 215, 403-410.
3. Bankevich, A., Nurk, S., Antipov, D., Gurevich, A. A., Dvorkin, M., Kulikov, A. S., Lesin, V. M., Nikolenko, S. I., Pham, S., Prjibelski, A. D., et al. (2012). SPAdes: a new genome assembly algorithm and its applications to single-cell sequencing. J. Comput. Biol. 19, 455-477.
4. Barrett, K., and Lange, L. (2019). Peptide-based functional annotation of carbohydrate-active enzymes by conserved unique peptide patterns (CUPP). Biotechnol. Biofuels 12, 102.
5. Beck, J. M., Schloss, P. D., Venkataraman, A., Twigg, H., 3rd, Jablonski, K. A., Bushman, F. D., Campbell, T. B., Charlson, E. S., Collman, R. G., Crothers, K., et al. (2015). Multicenter Comparison of Lung and Oral Microbiomes of HIV-infected and HIV-uninfected Individuals. Am. J. Respir. Crit. Care Med. 192, 1335-1344.
6. Belting, M. (2003). Heparan sulfate proteoglycan as a plasma membrane carrier. Trends Biochem. Sci. 28, 145-151.

7. Bolger, A. M., Lohse, M., and Usadel, B. (2014). Trimmomatic: a flexible trimmer for Illumina sequence data. Bioinformatics 30, 2114-2120.
8. Borodulin, K., Vartiainen, E., Peltonen, M., Jousilahti, P., Juolevi, A., Laatikainen, T., Männistö, S., Salomaa, V., Sundvall, J., and Puska, P. (2015). Forty-year trends in cardiovascular risk factors in Finland. Eur. J. Public Health 25, 539-546.
9. Cagno, Cagno, Tseligka, Jones, and Tapparel (2019). Heparan Sulfate Proteoglycans and Viral Attachment: True Receptors or Adaptation Bias? Viruses 11, 596.
10. Cartmell, A., Lowe, E. C., Basle, A., Firbank, S. J., Ndeh, D. A., Murray, H., Terrapon, N., Lombard, V., Henrissat, B., Turnbull, J. E., et al. (2017). How members of the human gut microbiota overcome the sulfation problem posed by glycosaminoglycans. Proc. Natl. Acad. Sci. U.S.A. 114, 7037-7042.
11. Chen, Y., Maguire, T., Hileman, R. E., Fromm, J. R., Esko, J. D., Linhardt, R. J., and Marks, R. M. (1997). Dengue virus infectivity depends on envelope protein binding to target cell heparan sulfate. Nat. Med. 3, 866-871.
12. Chen, Y., Götte, M., Liu, J., and Park, P. W. (2008). Microbial subversion of heparan sulfate proteoglycans. Mol. Cells 26, 415-426.
13. Church, D. M., Schneider, V. A., Graves, T., Auger, K., Cunningham, F., Bouk, N., Chen, H.-C., Agarwala, R., McLaren, W. M., Ritchie, G. R. S., et al. (2011). Modernizing reference genome assemblies. PLoS Biol. 9, e1001091.
14. Claesson, M. J., Cusack, S., O'Sullivan, O., Greene-Diniz, R., de Weerd, H., Flannery, E., Marchesi, J. R., Falush, D., Dinan, T., Fitzgerald, G., et al. (2011). Composition, variability, and temporal stability of the intestinal microbiota of the elderly. Proc. Natl. Acad. Sci. U.S.A. 108 *Suppl* 1, 4586-4591.
15. Clausen, T. M., Sandoval, D. R., Spliid, C. B., Pihl, J., Painter, C. D., Thacker, B. E., Glass, C. A., Narayanan, A., Majowicz, S. A., Zhang, Y., et al. (2020). SARS-CoV-2 Infection Depends on Cellular Heparan Sulfate and ACE2. Cell 83:1043-1057.
16. Connell, B. J., and Lortat-Jacob, H. (2013). Human immunodeficiency virus and heparan sulfate: from attachment to entry inhibition. Front. Immunol. 4, 385.
17. Davies, N. G., Klepac, P., Liu, Y., Prem, K., Jit, M., Eggo, R. M., Group, C. C.-19 W., and Others (2020). Age-dependent effects in the transmission and control of COVID-19 epidemics. MedRxiv.
18. de la Cuesta-Zuluaga, J., Kelley, S. T., Chen, Y., Escobar, J. S., Mueller, N. T., Ley, R. E., McDonald, D., Huang, S., Swafford, A. D., Knight, R., et al. (2019). Age- and sex-dependent patterns of gut microbial diversity in human adults. mSystems 4.
19. Didion, J. P., Martin, M., and Collins, F. S. (2017). Atropos: specific, sensitive, and speedy trimming of sequencing reads. PeerJ 5, e3720.
20. Eilam, O., Zarecki, R., Oberhardt, M., Ursell, L. K., Kupiec, M., Knight, R., Gophna, U., and Ruppin, E. (2014). Glycan degradation (GlyDeR) analysis predicts mammalian gut microbiota abundance and host diet-specific adaptations. mBio 5.
21. Esko, J. D., and Selleck, S. B. (2002). Order out of chaos: assembly of ligand binding sites in heparan sulfate. Annu. Rev. Biochem. 71, 435-471.
22. Galkin, F., Mamoshina, P., Aliper, A., Putin, E., Moskalev, V., Gladyshev, V. N., and Zhavoronkov, A. (2020).

Human Gut Microbiome Aging Clock Based on Taxonomic Profiling and Deep Learning. iScience 23, 101199.

23. Galliher, P. M., Cooney, C. L., Langer, R., and Linhardt, R. J. (1981). Heparinase production by *Flavobacterium heparinum*. Appl. Environ. Microbiol. 41, 360-365.

24. Geva-Zatorsky, N., Sefik, E., Kua, L., Pasman, L., Tan, T. G., Ortiz-Lopez, A., Yanortsang, T. B., Yang, L., Jupp, R., Mathis, D., et al. (2017) Mining the Human Gut Microbiota for Immunomodulatory Organisms. Cell 168, 928-943. e11.

25. Giroglou, T., Florin, L., Schafer, F., Streeck, R. E., and Sapp, M. (2001). Human papillomavirus infection requires cell surface heparan sulfate. J. Virol. 75, 1565-1570.

26. Grondin, J. M., Tamura, K., Déjean, G., Abbott, D. W., and Brumer, H. (2017). Polysaccharide Utilization Loci: Fueling Microbial Communities. J. Bacteriol. 199.

27. Haiminen, N., Utro, F., Seabolt, E., and Parida, L. (2020). Functional pathways in respiratory tract microbiome separate COVID-19 from community-acquired pneumonia patients. BioRxiv. doi: https://doi.org/10.1101/2020.05.01.073171.

28. Hillmann, B., Al-Ghalith, G. A., Shields-Cutler, R. R., Zhu, Q., Gohl, D. M., Beckman, K. B., Knight, R., and Knights, D. (2018). Evaluating the Information Content of Shallow Shotgun Metagenomics. mSystems 3.

29. Human Microbiome Project Consortium (2012). Structure, function and diversity of the healthy human microbiome. Nature 486, 207-214.

30. Hobbs, J. K., Pluvinage, B., and Boraston, A. B. (2018). Glycan-metabolizing enzymes in microbe-host interactions: the *Streptococcus pneumoniae* paradigm. FEBS Lett. 592, 3865-3897.

31. Hoffmann, M., Kleine-Weber, H., Schroeder, S., Krüger, N., Herrler, T., Erichsen, S., Schiergens, T. S., Herrler, G., Wu, N.-H., Nitsche, A., et al. (2020). SARS-CoV-2 Cell Entry Depends on ACE2 and TMPRSS2 and Is Blocked by a Clinically Proven Protease Inhibitor. Cell 181, 271-280. e8.

32. Huang, S., Haiminen, N., Carrieri, A.-P., Hu, R., Jiang, L., Parida, L., Russell, B., Allaband, C., Zarrinpar, A., Vázquez-Baeza, Y., et al. (2020). Human Skin, Oral, and Gut Microbiomes Predict Chronological Age. mSystems 5.

33. Iba, T., and Levy, J. H. (2019). Derangement of the endothelial glycocalyx in sepsis. J. Thromb. Haemost. 17, 283-294.

34. Kanehisa, M., Furumichi, M., Tanabe, M., Sato, Y., and Morishima, K. (2017). KEGG: new perspectives on genomes, pathways, diseases and drugs. Nucleic Acids Res. 45, D353-D361.

35. Kim, S. Y., Jin, W., Sood, A., Montgomery, D. W., Grant, O. C., Fuster, M. M., Fu, L., Dordick, J. S., Woods, R. J., Zhang, F., et al. (2020). Characterization of heparin and severe acute respiratory syndrome-related coronavirus 2 (SARS-CoV-2) spike glycoprotein binding interactions. Antiviral Res. 104873.

36. Koenig, J. E., Spor, A., Scalfone, N., Fricker, A. D., Stombaugh, J., Knight, R., Angenent, L. T., and Ley, R. E. (2011). Succession of microbial consortia in the developing infant gut microbiome. Proc. Natl. Acad. Sci. U.S.A. 108 *Suppl* 1, 4578-4585.

37. Lagesen, K., Hallin, P., Rødland, E. A., Staerfeldt, H.-H., Rognes, T., and Ussery, D. W. (2007). RNAmmer consistent and rapid annotation of ribosomal RNA genes. Nucleic Acids Res. 35, 3100-3108.

38. Lang, J., Yang, N., Deng, J., Liu, K., Yang, P., Zhang, G., and Jiang, C. (2011). Inhibition of SARS pseudovirus cell entry by lactoferrin binding to heparan sulfate proteoglycans. PLoS One 6, e23710.

39. Langmead, B., and Salzberg, S. L. (2012). Fast gapped-read alignment with Bowtie 2. Nat. Methods 9, 357-359.

40. Lee, I., Ouk Kim, Y., Park, S.-C., and Chun, J. (2016). OrthoANI: An improved algorithm and software for calculating average nucleotide identity. Int. J. Syst. Evol. Microbiol. 66, 1100-1103.

41. Linhardt, R. J., Galliher, P. M., and Cooney, C. L. (1986). Polysaccharide lyases. Appl. Biochem. Biotechnol. 12, 135-176.

42. Lloyd-Price, J., Mahurkar, A., Rahnavard, G., Crabtree, J., Orvis, J., Hall, A. B., Brady, A., Creasy, H. H., McCracken, C., Giglio, M. G., et al. (2017). Erratum: Strains, functions and dynamics in the expanded Human Microbiome Project. Nature 551, 256.

43. Lombard, V., Golaconda Ramulu, H., Drula, E., Coutinho, P. M., and Henrissat, B. (2014). The carbohydrate-active enzymes database (CAZy) in 2013. Nucleic Acids Res. 42, D490-D495.

44. Magoč, T., and Salzberg, S. L. (2011). FLASH: fast length adjustment of short reads to improve genome assemblies. Bioinformatics 27, 2957-2963.

45. McDonald, D., Hyde, E., Debelius, J. W., Morton, J. T., Gonzalez, A., Ackermann, G., Aksenov, A. A., Behsaz, B., Brennan, C., Chen, Y., et al. (2018). American Gut: an Open Platform for Citizen Science Microbiome Research. mSystems 3.

46. Mycroft-West, C., Su, D., Elli, S., Li, Y., Guimond, S., Miller, G., Turnbull, J., Yates, E., Guerrini, M., Fernig, D., et al. The 2019 coronavirus (SARS-CoV-2) surface protein (Spike) S1 Receptor Binding Domain undergoes conformational change upon heparin binding. BioRxiv. doi: https://doi.org/10.1101/2020.02.29.971093.

47. Ndeh, D., Baslé, A., Strahl, H., Yates, E. A., McClurgg, U. L., Henrissat, B., Terrapon, N., and Cartmell, A. (2020). Metabolism of multiple glycosaminoglycans by *Bacteroides thetaiotaomicron* is orchestrated by a versatile core genetic locus. Nat. Commun. 11, 646.

48. Ndeh, D., Rogowski, A., Cartmell, A., Luis, A. S., Basle, A., Gray, J., Venditto, I., Briggs, J., Zhang, X., Labourel, A., et al. (2017). Complex pectin metabolism by gut bacteria reveals novel catalytic functions. Nature 544, 65-70.

49. Pavlova, S. I., Wilkening, R. V., Federle, M. J., Lu, Y., Schwartz, J., and Tao, L. (2019). *Streptococcus endopeptidases* promote HPV infection in vitro. Microbiologyopen 8, e00628.

50. Pfeiffer, J. K., and Virgin, H. W. (2016). Viral immunity. Transkingdom control of viral infection and immunity in the mammalian intestine. Science 351.

51. Poore, G. D., Kopylova, E., Zhu, Q., Carpenter, C., Fraraccio, S., Wandro, S., Kosciolek, T., Janssen, S., Metcalf, J., Song, S. J., et al. (2020). Microbiome analyses of blood and tissues suggest cancer diagnostic approach. Nature 579, 567-574.

52. Pruitt, K. D., Tatusova, T., and Maglott, D. R. (2007). NCBI reference sequences (RefSeq): a curated non-redundant sequence database of genomes, transcripts and proteins. Nucleic Acids Res. 35, D61-D65.

53. Richelle, A., Joshi, C., and Lewis, N. E. (2018). Assessing key decisions for transcriptomic data integration in biochemical networks. PLoS Comput Biol 15(7): e1007185. https://doi.org/10.1371/journal.pcbi.1007185

54. Richelle, A., Chiang, A. W. T., Kuo, C.-C., and Lewis, N. E. (2019). Increasing consensus of context-specific metabolic models by integrating data-inferred cell functions. PLoS Comput. Biol. 15, e1006867.

55. Richelle, A., Kellman, B. P., Wenzel, A. T., Chiang, A. W. T., Reagan, T., Gutierrez, J. M., Joshi, C., Li, S., Liu, J. K., Masson, H., et al. (2020). What does your cell really do? Model-based assessment of mammalian cells metabolic functionalities using omics data.

56. Robb, M., Hobbs, J. K., Woodiga, S. A., Shapiro-Ward, S., Suits, M. D. L., McGregor, N., Brumer, H., Yesilkaya, H., King, S. J., and Boraston, A. B. (2017). Molecular Characterization of N-glycan Degradation and Transport in Streptococcus pneumoniae and Its Contribution to Virulence. PLOS Pathogens 13, e1006090.

57. Salosensaari, A., Laitinen, V., Havulinna, A. S., Meric, G., Cheng, S., Perola, M., Valsta, L., Alfthan, G., Inouye, M., Watrous, J. D., et al. (2020). Taxonomic Signatures of Long-Term Mortality Risk in Human Gut Microbiota. medRxiv. doi: https://doi.org/10.1101/2019.12.30.19015842.

58. Sanders, J. G., Nurk, S., Salido, R. A. Minich, J., Zhenjiang, Z. X., Qiyun, Z., Martino, C., Fedarko, M., Arthur, T. D., Chen, F., et al. (2019). Optimizing sequencing protocols for leaderboard metagenomics by combining long and short reads. Genome Biol 20, 226. https://doi.org/10.1186/s13059-019-1834-9

59. Schneider, V. A., Graves-Lindsay, T., Howe, K., Bouk, N., Chen, H.-C., Kitts, P. A., Murphy, T. D., Pruitt, K. D., Thibaud-Nissen, F., Albracht, D., et al. (2017). Evaluation of GRCh38 and de novo haploid genome assemblies demonstrates the enduring quality of the reference assembly. Genome Res. 27, 849-864.

60. Schulze, A., Gripon, P., and Urban, S. (2007). Hepatitis B virus infection initiates with a large surface protein-dependent binding to heparan sulfate proteoglycans. Hepatology 46, 1759-1768.

61. Shen, Z., Xiao, Y., Kang, L., Ma, W., Shi, L., Zhang, L., Zhou, Z., Yang, J., Zhong, J., Yang, D., et al. (2020). Genomic diversity of SARS-CoV-2 in Coronavirus Disease 2019 patients. Clin. Infect. Dis. 71, 713-720.

62. Spear, P. G., Shieh, M. T., Herold, B. C., WuDunn, D., and Koshy, T. I. (1992). Heparan sulfate glycosaminoglycans as primary cell surface receptors for herpes simplex virus. Adv. Exp. Med. Biol. 313, 341-353.

63. Terrapon, N., Lombard, V., Gilbert, H. J., and Henrissat, B. (2015). Automatic prediction of polysaccharide utilization loci in Bacteroidetes species. Bioinformatics 31, 647-655.

64. Terrapon, N., Lombard, V., Drula, É., Lapébie, P., Al-Masaudi, S., Gilbert, H. J., and Henrissat, B. (2018). PULDB: the expanded database of Polysaccharide Utilization Loci. Nucleic Acids Res. 46, D677-D683.

65. Thaiss, C. A., Zmora, N., Levy, M., and Elinav, E. (2016). The microbiome and innate immunity. Nature 535, 65-74.

66. Toledo, A. G., Golden, G., Campos, A. R., Cuello, H., Sorrentino, J., Lewis, N., Varki, N., Nizet, V., Smith, J. W., and Esko, J. D. (2019). Proteomic atlas of organ vasculopathies triggered by Staphylococcus aureus sepsis. Nat. Commun. 10, 4656.

67. Trottein, F., and Sokol, H. (2020). Potential Causes and Consequences of Gastrointestinal Disorders during a SARS-CoV-2 Infection. Cell Rep. 107915.

68. Ulmer, J. E., Vilén, E. M., Namburi, R. B., Benjdia, A., Beneteau, J., Malleron, A., Bonnaffé, D., Driguez, P.-A., Descroix, K., Lassalle, G., et al. (2014). Characterization of glycosaminoglycan (GAG) sulfatases from the human gut symbiont Bacteroides thetaiotaomicron reveals the first GAG-specific bacterial endosulfatase. J. Biol. Chem. 289, 24289-24303.

69. Virtanen, P., Gommers, R., Oliphant, T. E., Haberland, M., Reddy, T., Cournapeau, D., Burovski, E., Peterson, P., Weckesser, W., Bright, J., et al. (2020). SciPy 1.0: fundamental algorithms for scientific computing in Python. Nat. Methods 17, 261-272.

70. Walls, A. C., Park, Y.-J., Tortorici, M. A., Wall, A., McGuire, A. T., and Veesler, D. (2020). Structure, Function, and Antigenicity of the SARS-CoV-2 Spike Glycoprotein. Cell. 181, 281-292.

71. Weiss, R. J., Esko, J. D., and Tor, Y. (2017). Targeting heparin and heparan sulfate protein interactions. Org Biomol Chem 15, 5656-5668.

72. Williamson, E. J., Walker, A. J., Bhaskaran, K., Bacon, S., Bates, C., Morton, C. E., Curtis, H. J., Mehrkar, A., Evans, D., Inglesby, P., et al. (2020). OpenSAFELY: factors associated with COVID-19 death in 17 million patients. Nature.

73. Yin, Y., Mao, X., Yang, J., Chen, X., Mao, F., and Xu, Y. (2012). dbCAN: a web resource for automated carbohydrate-active enzyme annotation. Nucleic Acids Res. 40, W445-W451.

74. Zhang, H., Yohe, T., Huang, L., Entwistle, S., Wu, P., Yang, Z., Busk, P. K., Xu, Y., and Yin, Y. (2018). dbCAN2: a meta server for automated carbohydrate-active enzyme annotation. Nucleic Acids Res. 46, W95-W101.

75. Zhou, P., Yang, X.-L., Wang, X.-G., Hu, B., Zhang, L., Zhang, W., Si, H.-R., Zhu, Y., Li, B., Huang, C.-L., et al. (2020). A pneumonia outbreak associated with a new coronavirus of probable bat origin. Nature 579, 270-273.

76. Zhu, Q., Mai, U., Pfeiffer, W., Janssen, S., Asnicar, F., Sanders, J. G., Belda-Ferre, P., Al-Ghalith, G. A., Kopylova, E., McDonald, D., et al. (2019). Phylogenomics of 10,575 genomes reveals evolutionary proximity between domains Bacteria and Archaea. Nat. Commun. 10, 5477.

77. Zuo, T., Zhang, F., Lui, G. C. Y., Yeoh, Y. K., Li, A. Y. L., Zhan, H., Wan, Y., Chung, A., Cheung, C. P., Chen, N., et al. (2020). Alterations in Gut Microbiota of Patients With COVID-19 During Time of Hospitalization. Gastroenterology. doi: https://doi.org/10.1053/j.gastro.2020.05.048.

Sources for Heparan Sulfate Modification Capability Prediction

78. Richelle, A., Joshi, C., and Lewis, N. E. (2018). Assessing key decisions for transcriptomic data integration in biochemical networks. PLoS Comput Biol 15(7): e1007185. https://doi.org/10.1371/journal.pcbi.1007185

79. Richelle, A., Chiang, A. W. T., Kuo, C.-C., and Lewis, N. E. (2019). Increasing consensus of context-specific metabolic models by integrating data-inferred cell functions. PLoS Comput. Biol. 15, e1006867.

80. Richelle, A., Kellman, B. P., Wenzel, A. T., Chiang, A. W. T., Reagan, T., Gutierrez, J. M., Joshi, C., Li, S., Liu, J. K., Masson, H., et al. (2020). What does your cell really do? Model-based assessment of mammalian cells metabolic functionalities using omics data.

81. Kanehisa, M., Furumichi, M., Tanabe, M., Sato, Y., and Morishima, K. (2017). KEGG: new perspectives on genomes, pathways, diseases and drugs. Nucleic Acids Res. 45, D353-D361.

82. Hobbs, J. K., Pluvinage, B., and Boraston, A. B. (2018). Glycan-metabolizing enzymes in microbe-host interactions: the *Streptococcus pneumoniae* paradigm. FEBS Lett. 592, 3865-3897.

83. Robb, M., Hobbs, J. K., Woodiga, S. A., Shapiro-Ward, S., Suits, M. D. L., McGregor, N., Brumer, H., Yesilkaya, H., King, S. J., and Boraston, A. B. (2017). Molecular Characterization of N-glycan Degradation and Transport in *Streptococcus pneumoniae* and Its Contribution to Virulence. PLOS Pathogens 13, e1006090.

84. Ndeh, D., Baslé, A., Strahl, H., Yates, E. A., McClurgg, U. L., Henrissat, B., Terrapon, N., and Cartmell, A. (2020). Metabolism of multiple glycosaminoglycans by *Bacteroides thetaiotaomicron* is orchestrated by a versatile core genetic locus. Nat. Commun. 11, 646.

85. Ndeh, D., Rogowski, A., Cartmell, A., Luis, A. S., Basle, A., Gray, J., Venditto, I., Briggs, J., Zhang, X., Labourel, A., et al. (2017). Complex pectin metabolism by gut bacteria reveals novel catalytic functions. Nature 544, 65-70.

86. Barrett, K., and Lange, L. (2019). Peptide-based functional annotation of carbohydrate-active enzymes by conserved unique peptide patterns (CUPP). Biotechnol. Biofuels 12, 102.

87. Lombard, V., Golaconda Ramulu, H., Drula, E., Coutinho, P. M., and Henrissat, B. (2014). The carbohydrate-active enzymes database (CAZy) in 2013. Nucleic Acids Res. 42, D490-D495.

88. Magoč, T., and Salzberg, S. L. (2011). FLASH: fast length adjustment of short reads to improve genome assemblies. Bioinformatics 27, 2957-2963.

89. Yin, Y., Mao, X., Yang, J., Chen, X., Mao, F., and Xu, Y. (2012). dbCAN: a web resource for automated carbohydrate-active enzyme annotation. Nucleic Acids Res. 40, W445-W451.

90. Zhang, H., Yohe, T., Huang, L., Entwistle, S., Wu, P., Yang, Z., Busk, P. K., Xu, Y., and Yin, Y. (2018). dbCAN2: a meta server for automated carbohydrate-active enzyme annotation. Nucleic Acids Res. 46, W95-W101.

What is claimed is:

1. A method of degrading heparan sulfate comprising administering an effective amount of a composition comprising heparin lyase or a heparin lyase-producing microbe, wherein administration blocks SARS-COV-2 spike protein binding to a mammalian cell surface heparan sulfate.

2. The method of claim 1, wherein the heparin lyase-producing microbe is *B. ovatus* or *B. thetaiotaomicron*.

3. The method of claim 1, wherein the heparin lyase-producing microbe is genetically engineered to produce heparin lyase.

4. The method of claim 3, wherein the heparin lyase-producing microbe is an *Escherichia coli* Nissle (EcN).

5. The method of claim 1, wherein the heparin lyase is obtained from a supernatant of a culture of *B. ovatus, B. thetaiotaomicron*, or *Flavobacterium heparinum*.

* * * * *